United States Patent [19]

Leistner et al.

[11] Patent Number: 5,362,881
[45] Date of Patent: Nov. 8, 1994

[54] COUPLED BENZOTRIAZOLE AND BENZOPHENONE UV ABSORBERS

[75] Inventors: William E. Leistner, Atlantic Beach, N.Y.; Semyon Moshchitsky, Old Bridge, N.J.

[73] Assignee: Fairmount Chemical Company, Inc., Newark, N.J.

[21] Appl. No.: 69,000

[22] Filed: May 27, 1993

[51] Int. Cl.$^5$ .............................................. C07D 249/20
[52] U.S. Cl. ..................................... 548/260; 548/259
[58] Field of Search .............................. 548/259, 260

[56] References Cited

U.S. PATENT DOCUMENTS

| | | | |
|---|---|---|---|
| 4,186,151 | 1/1980 | Kubota et al. | 260/591 |
| 4,684,679 | 8/1987 | Kubota et al. | 524/91 |
| 4,812,498 | 3/1989 | Nakahara et al. | 524/91 |
| 4,937,348 | 6/1990 | Kubota | 548/259 |
| 4,943,637 | 7/1990 | Seino et al. | 548/260 |
| 5,099,027 | 3/1992 | Vogl et al. | 548/259 |
| 5,104,992 | 4/1992 | Fukuoka et al. | 548/260 |

FOREIGN PATENT DOCUMENTS 1670951  2/1971  Germany .

*Primary Examiner*—Patricia L. Morris
*Attorney, Agent, or Firm*—Richard S. Roberts

[57] ABSTRACT

Provided are ultraviolet stabilizers which are diphenylmethane compounds of the formula:

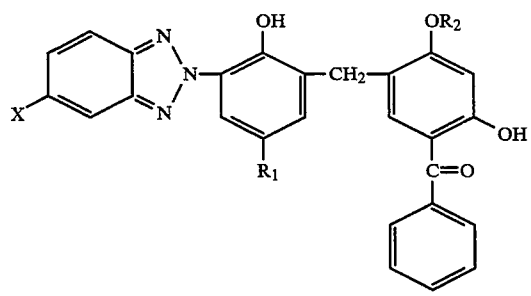

wherein:

$R_1$ and $R_2$ are independently $C_1$ to $C_8$ alkyl, cyclopentyl, cyclohexyl or cumyl; and X is selected from the group consisting of hydrogen, halogen, $C_1$ to $C_{12}$ alkyl and $C_1$ to $C_{12}$ alkoxy. The invention also pertains to a process for their preparation and stabilized polymer blends containing the stabilizers.

18 Claims, No Drawings

COUPLED BENZOTRIAZOLE AND BENZOPHENONE UV ABSORBERS

BACKGROUND OF THE INVENTION

The invention relates to ultraviolet light absorbers useful as stabilizers for plastics and coating compositions. More particularly, the invention concerns coupled compounds which contain both benzotriazole and benzophenone parts, which are u.v. light stabilizers.

A problem in the art of manufacturing and processing thermoplastic polymers and coating compositions is their instability upon extended exposure to ultraviolet light sources. It is well known that light, oxygen and heat cause degradation of polymers resulting in deterioration of mechanical and physical properties of the polymer. Coatings and plastics tend to demonstrate unwanted color changes and reduced mechanical strength upon exposure to uv radiation. For example, in the case of polyvinyl chloride, it is theorized that ultraviolet exposure results in the formation of free radicals on the polymer chain which react with atmospheric oxygen. The resulting peroxide groups are in such a position that they activate a chlorine atom giving rise to a weak spot on the polymer. Irradiation in the presence of oxygen causes the molecular weight to decrease and is indicative of chain scission. Irradiation in the absence of oxygen causes an increase in molecular weight due to crosslinking. It is well known that polymer exposure to ultraviolet radiation will cause discoloration and brittleness, thus destroying its physical properties. To prevent or at least retard the damage caused by these factors, stabilizers are added to the plastic.

Various attempts have been made to improve resistance to deterioration by the introduction of uv stabilizers which are radiation absorbing. Light stabilizers are compounds which when added to the polymer are capable of interfering with the reactions of degradation caused by light energy. There are several classes of compounds which are used commercially for this purpose, the more important being 2-hydroxyphenyl benzotriazoles and benzophenones. It is generally accepted that 2-hydroxyphenyl benzotriazoles and benzophenones function as u.v. light stabilizers through the hydrogen bonding of the ortho hydroxy phenyl groups absorbing photons and dissipating it as harmless heat energy. There are many patents covering the manufacture and use of these u.v. absorbers in polymers and coatings. Both classes of compounds are themselves stable to both heat and light during long term exposure.

Although many stabilizers are known in the art, none are completely satisfactory in performance. The absorption of light by polymers is dependent on its chemical structure. Saturated plastics do not absorb above 250 nm. However, the presence of double bonds or chromophores causes the absorption to shift to higher wavelengths. Carbonyl structures absorb above 290 nm.

The presence of impurities such as catalyst residues, oxidation by-products, plasticizers and other stabilizers may cause the polymer to absorb at higher wavelengths. U.V. light is also capable of breaking chemical bonds in polymers which changes the absorption characteristics of the polymer. Polymers are degrade, by radiation with wavelengths of less than 325 nanometers. Threshold u.v. wavelengths for various chemical bonds below which bonds will break are C—N at 392.7 nm, C—Cl at 352.0 nm, C—C at 346.1 nm, S—H at 344.5 nm, N—H at 336.4 nm, C—O at 334.4 nm and C—H at 289.7 nm. The wavelength regions for the u.v. light types are UV-A at 320 to 400 nm which causes polymer degradation, causes suntan but no sunburn, and is transmitted by window glass. UV-B at 280 to 320 nm, which has the shortest wavelengths at the surface of the earth, is responsible for the most polymer damage, causes sunburn and is absorbed by window glass. UV-C, below 280 nm is found only in outer space or as produced by artificial light sources. It can be filtered out by ozone in the atmosphere and can cause abnormal reactions. Degradation also takes place at higher wavelengths but to a lesser degree. Commercial ultraviolet absorbers absorb radiation in a range between 290 and 400 nanometers. A definite yellowing of the polymer results when the ultraviolet absorber absorbs above 400 nanometers. The activation spectra for various polymers and the wavelengths of maximum damage are: polyvinyl acetate film <280 nm; polycarbonate film at 285 nm, 305 nm, 330 nm and 360 nm; acrylics at 290 nm and 325 nm; SAN film at 290 nm and 325 nm; CAB film at 295 nm and 298 nm; polyethylene at 300 nm; polypropylene at 310 nm and 370 nm, PVC at 320 nm; polyester at 325 nm and PVC/vinyl acetate at 327 nm and 364 nm.

There are other considerations when choosing a suitable u.v light stabilizer. Compatibility is one of them. Many stabilizers prove to be incompatible with the polymer or coating composition being stabilized. This is usually a function of its solubility in the polymer and can be indirectly measured by determining the solubility of the polymer in organic solvents. The higher the solubility in organic solvents, the greater the probability of compatibility in the polymer. Incomplete or poor solubility causes a lower absorbance than the theoretical value. It also results in exudation of the u.v. light absorber to the polymer surface. Another important consideration is the volatility of the stabilizer in the polymer and during processing. The stabilizer must have sufficiently high molecular weight so that it remains in the polymer matrix for the life of the plastic. Many polymers are processed at very high temperatures which causes the stabilizer to vaporize. Not only is some of the stabilizer lost to the atmosphere and not available to the polymer, but the working conditions require workers to wear gas masks and protective gear during processing. This creates a serious health hazard. Manufacturers have sought to solve the volatility problem by increasing the molecular weight of the u.v. absorber. To improve the solubility and reduce the volatility, appropriate side chains have been added to the u.v. light absorber molecule. This was usually done by adding various chemical groups to the phenolic ring or the benzene ring of the benzotriazole and benzophenone. In most cases, the additional molecular weight does not contribute to the light absorption properties of the u.v. light stabilizer. It does not enhance ability to change the absorbed photons to harmless dissipated heat. Since such groups usually do not contain chromophores, the u.v. absorption properties of the modified u.v. light absorber not only are not enhanced, they actually reduce the absorption. The additional problems of the rate of diffusion through the composition and the rate of loss of the stabilizer from the composition must be empirically determined and are not generally predictable.

In particular, it is known that some 2-hydroxy-4-alkoxybenzophenones are useful uv absorbers and light stabilizers. U.S. Pat. Nos. 3,399,237 and 3,310,525 show compounds having a plurality of benzophenone functional groups. U.S. Pat. No. 4,186,151 mentions symmetrical and asymmetrical 5, 5'-methylenebis(2-hydroxy-4-alkoxybenzophenone) compounds, but it cites no examples of asymmetrical compounds. Hydroxyphenyl benzotriazole monomers and dimers are also known to be uv absorbing. Monomers are disclosed in U.S. Pat. Nos. 5,097,041, 4,943,637 and 5,104,992. U.S. Pat. Nos. 4,684,679; 4,937,348 and 4,812,498 disclose symmetrical hydroxyphenyl benzotriazole dimers. All of these patents are incorporated herein by reference.

There are only a relatively few benzophenones and benzotriazoles which are effective stabilizers for plastics and coatings. All have very different properties with regard to solubility, melting point, molecular weight, uv absorption, and polymer compatibility and therefore, it is often impossible to select a given benzophenone or benzotriazole having the best combination of properties for the polymer or coating composition of choice. While it may be desired for a given stabilizer to have a certain uv absorption characteristic or melting point, it may not be compatible with the plastic preference. The hydroxyphenyl benzotriazoles possess the more desirable overall absorption characteristics since they absorb very strongly throughout most of the u.v. region and very little as the wavelength approaches 400 nm.

It has now been found that the volatility of benzotriazole and benzophenone stabilizers can be sharply reduced by coupling different u.v. light absorbing chemical moieties by utilizing methylene bridge processes. This route is highly selective in producing u.v. light stabilizers in good yield and purity. It has been unexpectedly found, that by forming a coupled compound which has 2-hydroxy-4-alkoxybenzophenone and hydroxybenzotriazolylphenol moieties, an improved class of uv stabilizers is produced. Surprisingly, the coupled benzotriazole-benzophenone u.v. light stabilizers resulting for this invention have lower melting points, better solubility in organic solvents, and better compatibility in most polymers than could have been predicted. In addition, the u.v. light absorption spectrum of the products covers a wider wavelength band than either the benzotriazole or benzophenone alone. This opens the possibility to tailor make u.v. light stabilizers having absorption qualities fitted to the needs of the particular polymer. The melting point, molecular weight, and uv absorption properties can be adjusted to the requirements of the polymer of choice, since each moiety contributes its beneficial characteristics. It has also been found that in general, such coupled compounds are more soluble in organic solvents than the symmetrical dimers made from the same monomer constituents. As a result, they are more easily and more uniformly blended in the plastic or coating composition to be stabilized.

SUMMARY OF THE INVENTION

The invention provides a coupled diphenylmethane compound having the formula:

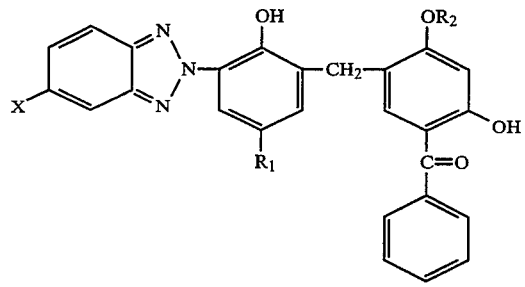

wherein:

$R_1$ and $R_2$ are independently $C_1$ to $C_8$ alkyl, cyclopentyl, cyclohexyl or cumyl; and X is selected from the group consisting of hydrogen, halogen, $C_1$ to $C_{12}$ alkyl and $C_1$ to $C_{12}$ alkoxy.

The invention also provides a stabilized polymer composition which comprises a polymeric compound and from about 0.1% to about 5% based on the weight of the polymeric composition of the above coupled compound.

The invention further provides a process for the preparation of a coupled diphenylmethane compound having the formula:

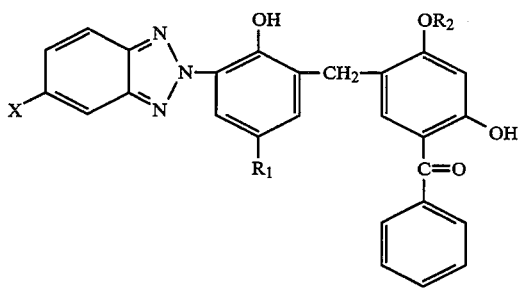

which comprises:

a.) reacting a 4-hydrocarbyl-6-benzotriazolylphenol having the formula:

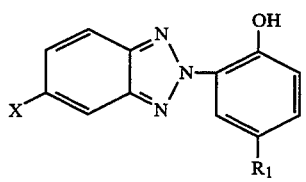

with an amine having the formula $HNR_3R_4$ and formaldehyde in an organic solvent to produce a Mannich base having the formula:

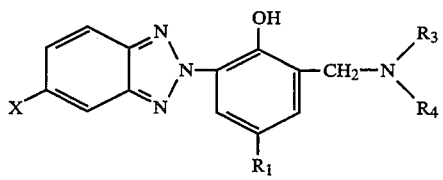

and b.) reacting the Mannich base, in the presence of an alkaline catalyst, with a 2-hydroxy-4-alkoxybenzophenone of the formula

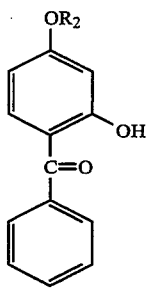

wherein $R_1$ and $R_2$ are independently $C_1$ to $C_8$ alkyl, cyclopentyl, cyclohexyl or cumyl;

X is selected from the group consisting of hydrogen, halogen, $C_1$ to $C_{12}$ alkyl and $C_1$ to $C_{12}$ alkoxy; and $R_3$ and $R_4$ are selected from the group consisting of $C_1$ to $C_6$ alkyl, and groups where $R_3$ and $R_4$ taken together form a four to six member heteroalicyclic ring including a nitrogen atom, provided that at least one of $R_3$ and $R_4$ is not hydrogen.

DETAILED DESCRIPTION OF THE PREFERRED EMBODIMENT

In the practice of the present invention one begins with a benzotriazole monomer of the formula

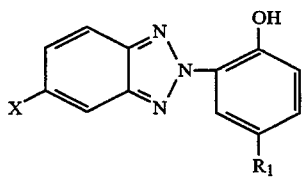

wherein $R_1$ is $C_1$ to $C_8$ alkyl, cyclopentyl, cyclohexyl or cumyl; and X is selected from the group consisting of hydrogen, halogen, $C_1$ to $C_{12}$ alkyl and $C_1$ to $C_{12}$ alkoxy. Hydroxyphenyl benzotriazole monomers may be prepared by any method known in the art including those taught in U.S. Pat. Nos. 5,097,041, 4,943,637 and 5,104,992. 2-aryl-2H-benzotriazoles monomers may be produced by reducing o-nitroazobenzenes through a 2-phenylbenzotriazole-N-oxide intermediate. A wide variety of reduction techniques is known. Reduction of o-nitroazobenzenes to 2-phenylbenzotriazole by zinc in the presence of sodium hydroxide is disclosed in U.S. Pat. Nos. 3,018,269; 3,230,194; 3,773,751; 4,041,044; and 4,224,451. Reduction using aldehyde reducing agents and aromatic ketone catalysts is disclosed in U.S. Pat. No. 4,835,284. Reduction using saccharides and an aromatic ketone catalyst is disclosed in U.S. Pat. No. 4,780,541. All of these patents are incorporated herein by reference. These show methods for the preparation of hydroxyphenyl benzotriazoles by reductive cyclization of azo dyes with saccharides in the presence of aromatic ketone catalysts, which act by receiving hydrogen from the reducing agent and giving hydrogen to a material to be reduced. In each of these cases, saccharide reduction is catalyzed by such aromatic ketone catalysts as substituted and unsubstituted fluorenone.

The coupled compounds of the present invention may be prepared by a two step process including first forming the Mannich base of the 4-hydrocarbyl-6-benzotriazolylphenol monomer, and then reacting the Mannich base with the 2-hydroxy-4-alkoxybenzophenone. The Mannich base is prepared by reacting the benzotriazole with an amine and formaldehyde in an organic solvent. The amines have the formula $HNR_3R_4$ and non-exclusively include such secondary alkyl amines as dimethylamine, diethylamine, di-n-propylamine, diisopropylamine, di-n-butylamine, di-t-butylamine, diisobutylamine, diamylamine, ethylmethylamine and ethyl-isopropylamine; and heteroalicyclic amines such as morpholine, piperidine and pyrrolidine. Formaldehyde or any of its polymeric forms can be used in the process of the invention such as gaseous formaldehyde, aqueous solutions of formaldehyde, paraformaldehyde, trioxane, trioxymethylene, tetraoxymethylene, and other solid polymers of formaldehyde. Importantly, the reverse reaction sequence does not work. That is, if one were first to form the Mannich base of the 2-hydroxy-4-alkoxybenzophenone and then react this product with the 4-hydrocarbyl-6-benzotriazolylphenol monomer, one does not obtain the coupled compounds of the present invention. Rather one obtains a symmetrical dimer of the benzophenone.

Solvents useful for this process step include essentially any inert organic solvent that is a solvent for the reactants. It also contemplated that solvents may be such as alcohols, ether hydrocarbons and halocarbons, among others. These include alcohols such as methanol, ethanol, isopropanol, and n-butanol, hydrocarbons such as hexane, heptane, benzene, toluene, xylene, petroleum ethers, and mineral spirits, cycloaliphatic ethers such as furan, tetrahydrofuran and dioxane. The amount of solvent is not critical and can range from about 50 to about 500 weight percent based on the amount of hydroxyphenyl benzotriazole. The amounts of amine and formaldehyde in the reaction with the hydroxyphenyl benzotriazole in the solvent can be stoichiometric or slightly more and preferably each is in the range of from about 1.0 to about 2.0 mole or more per mole of 4-hydrocarbyl-6benzotriazolylphenol. The Mannich base formation reaction can be carried out over a wide range of temperatures and is preferably from about 50° C. to about 150° C., or more preferably from about 80° C. to about 120° C. In the preferred embodiment, the reaction is preferably conducted for from about 2 hours to about 24 hours, or more preferably from about 6 hours to about 24 hours. The most advantageous reaction time and temperature may be determined by those skilled in the art.

The coupled compound production step is conducted by reacting the thusly produced Mannich base with a stoichiometric amount of the 2-hydroxy-4-alkoxybenzophenone. The coupled compound production reaction is preferably carried out in the presence of an alkaline catalyst. Such include lower alkali metal alcoholates such as sodium methylate and sodium ethylate, alkali metal hydroxides such as sodium and potassium hydroxide, and alkali metal alkaline salts such as potassium carbonate and sodium carbonate. The most preferred catalyst is sodium hydroxide. The amount of catalyst is not critical and preferably ranges from about 0.001 to about 50 parts by weight, or more preferably from about 0.01 to about 8 parts by weight per 100 parts of benzophenone. Preferably this reaction is carried out in an aromatic or aliphatic solvent having a boiling point of about 160° C. or above. The most preferred solvent is pseudocumene. The reaction can be carried out over a wide range of temperatures and is preferably from about 20° C. to about 200° C., or more preferably from about 30° C. to about 150° C. In the preferred embodiment, the coupled compound production reaction is conducted for from about 1 hours to about 24 hours, or more preferably from about 3 hours to about 12 hours. The most advantageous reaction time and temperature may be determined by those skilled in the art.

As hereinbefore mentioned, it is known in the art that polymers are unstable over time upon exposure to ultraviolet light. Such polymers non-exclusively include polycarbonates and their copolymers, polyacrylates and their copolymers, polyacetals, polystyrenes, polyacrylonitrile, polydienes, polyesters, polyamides, polyurethanes, acrylonitrile-butadiene-styrene resins, polyphenylene sulfide, fluorinated polymers, polyolefins, acrylonitrile polymers and copolymers, vinyl polymers and copolymers, vinylidene polymers and copolymers, polyvinylacetate and its copolymers, and cellulosic polymers, among others. The uv stability of such materials is improved by mixing the polymer with from about 0.1% to about 5 % based on the weight of the polymer composition of the coupled benzotriazole-benzophenone compounds of this invention. The composition may be formed by heating the polymer to its softening point in an extruder and adding the coupled compound to the melt to form a substantially uniform physical mixture. In the method of the invention, the polymer materials, which are thermoplastics or cellulosic materials and the coupled benzotriazole-benzophenone are blended in the desired quantities and heated to a temperature above the softening point of the polymer. The heating in an extruder and blending of the coupled compound are done as known in the art. The heating and blending can be done in either order, however, in the preferred embodiment, these processes are conducted simultaneously. The mixing may be conducted in any suitable equipment including a Banbury mixer, single or twin screw extruder, ribbon blender, injection molding machine, two roll mill or the like, thus forming a substantially uniform blend of the polymer material and the coupled compound. The mixing step is usually conducted for from about 0.1 minutes to about 10 minutes. In the preferred embodiment, the heating is conducted at a temperature of from about 100° F. to about 650° F., or more preferably from about 212° F. to about 600° F., and most preferably from about 300° F. to about 575° F.

The coupled compound of this invention can also be used as uv stabilizers for compositions such as organic coatings, and paints when blended with such additional components as solvents, colorants and binders. The following non-limiting examples serve to illustrate the invention.

EXAMPLE 1

[2-Dipropylaminomethyl,4,(1,1,3,3tetramethylbutyl)-6-(2H-benzotriazol-2-yl)phenol I. 323g (1 Mole) of [4-(1,1,3,3-tetramethylbutyl)-6-(2H-benzotriazol-2-yl)]phenol and 257 g (1.2 mole) of bis(dipropylamino) methane are dissolved in 500 ml of butanol-1 and the mixture is heated at reflux for 24 hours. The solvent is vacuum distilled off and product crystallized from acetonitrile. Yield 414g (95%). The melting point is 81.5° C.–83° C. and purity by HPLC is 99.8%.

II. 323g (1 Mole) of [4-(1,1,3,3-tetramethylbutyl)-6-(2H-benzotriazol-2-yl)]phenol, 42 g (1.4 mole) of paraformaldehyde, and 303g (3 mole) dipropylamine are dissolved in 500 ml of butanol-1 and the mixture heated at reflux for 20 hours. The solvent is vacuum distilled off and product crystallized from acetonitrile. Yield 98%.

III. 323 g (1 Mole) of [4-(1,1,3,3-tetramethylbutyl)-6-(2H-benzotriazol-2-yl)]phenol, 39 g (1.3 mole) of paraformaldehyde, and 303 g (3 mole) dipropylamine are heated with azeotropic removal of water and then the mixture is heated at 120° C.–125° C. for 20 hours. Dipropylamine is vacuum removed and the product crystallized from acetonitrile. Yield 396 (91%).

EXAMPLE 2

[2-Dimethylaminomethyl-4-methyl-6-(2H-benzotriazol-2-yl )]phenol

I. A mixture of 225 g (1 mole) of [4-methyl-6-(2H-benzotriazol-2-yl)] phenol, 248 g (2.2 mole) of 40% aqueous dimethylamine, 36 g (1.2 mole) of paraformaldehyde and 300 ml butanol-1 is heated at 85° C. to 90° C. with gentle reflux for 20 hours. The mixture is cooled to 10° C. The product is crystallized from acetonitrile to yield 211g (75%). The melting point is 93° C.–97° C.

II. A mixture of 225 g (1 mole) of [4-methyl-6-(2H-benzotriazol-2-yl)]phenol, 248 g (2.2 mole) of 40% aqueous dimethylamine, 36 g (1.2 mole) of paraformaldehyde and 300 ml isopropanol is heated in an autoclave at 120° C. and 50 psi pressure for 2 hours. The mixture is cooled to 10° C. The product is crystallized from acetonitrile to yield 87%.

EXAMPLE 3

[2,4'-Dihydroxy-3-(2H-benzotriazol-2-yl)-5-(1,1,3,3,-tetramethylbutyl)-2'-methoxy-5'-benzoyl]diphenylmethane 228g (1 Mole) of 2-hydroxy-4-methoxybenzophenone, 20 g (0.5 mole) of sodium hydroxide and 600 ml of pseudocumene are heated at 125° C. to 130° C. for 10 minutes and to this mixture is added 436 g (1 mole) of [2-dipropylaminomethyl-4-(1,1,3,3-tetramethylbutyl)-6-(2H-benzotriazol-2-yl)]phenol. The mixture is heated at 160° C. to 165° C. for 10 hours with constant distillation of water and dipropylamine. 100g of acetic acid are added, the mixture is heated at 130° C. to 135° C. for 15 minutes, and then 1500 ml of methanol are added. The mixture is cooled to 10° C. and a solid is filtered. The product is crystallized from methoxyethanol to yield 422g (75%). The melting point is 139.7° C.–141.2° C. and purity by HPLC is 99.7%.

EXAMPLE 4

[2,4'-Dihydroxy-3-(2H-benzotriazol-2-yl)-5-methyl-2'-n-octoxy-5'-benzoyl]diphenylmethane 326 g (1 Mole) of 2-hydroxy-4-n-octoxybenzophenone, 20 g (0.5 mole) of sodium hydroxide and 1,000 ml of pseudocumene are heated at 125° C. to 130° C. for 10 minutes and to this mixture is added 282g (1 mole) of [2-dimethylaminomethyl-4-methyl-6-(2H-benzotriazol-2yl)]phenol. The mixture is heated at 160° C. to 165° C. for 4 hours with constant removal of dimethylamine. Pseudocumene is vacuum distilled, 1,500 ml of methanol and 100 g of acetic acid are added, and the mixture is heated to reflux for 20 minutes. The mixture is cooled to 10° C. and a solid is filtered. The product is crystallized from methoxyethanol to yield 450 g (80%). The melting point is 119° C.–125° C. and purity by HPLC is 91%.

EXAMPLE 5

[2,4'-Dihydroxy-3-(2H-benzotriazol-2-yl)-5-methyl-2'-methoxy-5'-benzoyl]diphenylmethane 228 g (1 Mole) of 2-hydroxy-4-methoxybenzophenone, 20 g (0.5 mole) of sodium hydroxide and 1,000 ml of pseudocumene are heated at 165° C. for 10 minutes and to this mixture is added 282 g (1 mole) of [2-dimethylaminomethyl-4-methyl-6-(2H-benzotriazol-2yl)]-phenol. The mixture is heated at 160° C. to 165° C. for 4 hours with constant removing of dimethylamine. Pseudocumene is vacuum distilled, 1,500 ml of methanol and 100g of acetic acid are added, and the mixture is heated to reflux for 20 minutes. The mixture is cooled to 10° C. and a solid is filtered. The product is crystallized from methoxyethanol to yield 320 g (68%). The melting point is 213° C.-215° C. Purity by HPLC is 93.4%.

EXAMPLE 6

[2,4'-Dihydroxy-3-(2H-benzotriazol-2-yl)-5-(1,1,3,3-tetramethylbutyl)-2'-octoxy-5'-benzoyl]diphenylmethane 326g (1 Mole) of 2-hydroxy-4-n-octoxybenzophenone, 20g (0.5 mole) of sodium hydroxide and 600 ml of pseudocumene are heated at 125° C. to 130° C. for 10 minutes and to this mixture is added 436g (1 mole) of [2-dipropylaminomethyl-4-(1,1,3,3-tetramethylbutyl)-6-(2H-benzotriazol-2-yl)]phenol. The mixture is heated at 160° C. to 165° C. for 6 hours with constant distillation of water and dipropylamine. Pseudocumene is vacuum distilled, 1,500 ml of methanol and 100 g of acetic acid are added, and the mixture is heated to reflux for 20 minutes. The mixture is cooled to 10° C. and a solid is filtered. The product is crystallized from methoxyethanol to yield 515 g (78%). The melting point is 90° C.-91° C. and purity by HPLC is 95.1%.

EXAMPLE 7 (COMPARATIVE)

The mixture of 22.5g (0.1 mole) of 4-methyl-6-benzotriazol-2-yl-phenol, 2g (0.05 mole) of sodium hydroxide and 100 ml of pseudocumene is heated at 130°-140° C. for 10 minutes and to this mixture is added 28.5 g (0.1 mole) of 5-dimethylaminomethyl-2-hydroxy-4-methoxybenzophenone and the mixture is heated at 160°-165° C. for 10 hours. Pseudocumene is vacuum distilled and 150 ml of methanol and 10 ml of acetic acid are added. The isolated product is 5,5'-methylene-bis-(2-hydroxy-4-methoxybenzophenone). This melting point is 226°-229° C. This example demonstrates that the reaction of the Mannich base of the benzophenone compound with the benzotriazole compound does not produce the coupled compound of this invention, but rather produces a symmetrical dimer of the benzophenone compound.

EXAMPLE 8

The following table compares some physical properties of coupled benzotriazole and benzophenone derivatives.

TABLE 1

| COMPOUND | MOLECULAR WEIGHT | MELTING POINT °C. | SOLUBILITY IN SOLVENTS (POLAR AND NON-POLAR) AT 25° C., IN GRAMS PER 100 GM. SOLVENT | | | |
|---|---|---|---|---|---|---|
| | | | METHANOL (POLAR) (PROTONIC) | ACETONITRILE (POLAR) (APROTONIC) | DIMETHYL FORMAMIDE (POLAR) (APROTONIC) | PSEUDOCUMENE (NON-POLAR) |
| [2,4'-Dihydroxy-3-(2H-benzotriazol-2-yl)-5-methyl-2'-methoxy-5'-benzoyl]diphenylmethane | 465 | 213–215 | Insoluble | Insoluble | 0.65 | 0.55 |
| [2,4'-Dihydroxy-3-(2H-benzotriazol-2-yl)-5-methyl-2'-n-octoxy-5'-benzoyl]diphenylmethane | 563 | 119–125 | Insoluble | Insoluble | 3.65 | 10.55 |
| [2,4'-Dihydroxy-3-(2H-benzotriazol-2-yl)-5-t-octyl-2'-methoxy-5'-benzoyl]diphenylmethane | 563 | 139–141 | Insoluble | 0.85 | 14.1 | 21.2 |
| [2,4'-Dihydroxy-3-(2H-benzotriazol-2-yl)-5-t-octyl-2'-n-octoxy-5'-benzoyl]diphenylmethane | 661 | 90–91 | 0.16 | 0.16 | 6.89 | 49.1 |

What is claimed is:

1. A diphenylmethane compound having the formula:

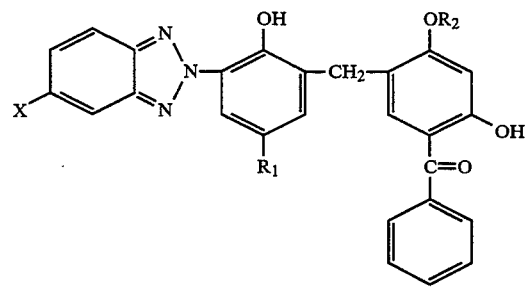

wherein:
$R_1$ and $R_2$ are independently $C_1$ to $C_8$ alkyl, cyclopentyl, cyclohexyl or cumyl; and
X is selected from the group consisting of hydrogen, halogen, $C_1$ to $C_{12}$ alkyl and $C_1$ to $C_{12}$ alkoxy.

2. The compound of claim 1 wherein $R_1$ is methyl and $R_2$ is methyl.

3. The compound of claim 1 wherein $R_1$ is t-octyl and $R_2$ is n-octyl.

4. The compound of claim 1 wherein $R_1$ is t-octyl and $R_2$ is methyl.

5. The compound of claim 1 wherein $R_1$ is methyl and $R_2$ is n-octyl.

6. The compound of claim 1 wherein X is hydrogen.

7. The compound of claim 2 wherein X is hydrogen.

8. The compound of claim 3 wherein X is hydrogen.

9. The compound of claim 4 wherein X is hydrogen.

10. The compound of claim 5 wherein X is hydrogen.

11. The compound of claim 1 wherein X is halogen.

12. The compound of claim 1 wherein X is $C_1$ to $C_{12}$ alkyl.

13. The compound of claim 1 wherein X is $C_1$ to $C_{12}$ alkoxy.

14. The compound of claim 1 wherein $R_1$ and $R_2$ are independently $C_1$ to $C_8$ alkyl.

15. The compound of claim 1 wherein $R_1$ and $R_2$ are independently $C_1$ to $C_8$ alkyl and wherein X is hydrogen.

16. The compound of claim 1 wherein $R_1$ and $R_2$ are independently $C_1$ to $C_8$ alkyl and wherein X is halogen.

17. The compound of claim 1 wherein $R_1$ and $R_2$ are independently $C_1$ to $C_8$ alkyl and wherein X is $C_1$ to $C_{12}$ alkyl.

18. The compound of claim 1 wherein $R_1$ and $R_2$ are independently $C_1$ to $C_8$ alkyl and wherein X is $C_1$ to $C_{12}$ alkoxy.

* * * * *